(12) United States Patent
Park et al.

(10) Patent No.: US 7,420,050 B2
(45) Date of Patent: Sep. 2, 2008

(54) TGF-β-SPECIFIC COVALENTLY CLOSED ANTISENSE MOLECULE

(75) Inventors: Jong-Gu Park, Daegu (KR); Ik-Jae Moon, Daegu (KR); Young-Kook Choi, Daegu (KR); Kwankyu Park, Daegu (KR)

(73) Assignee: Welgene Pharmaceuticals, Inc., Daegu (KR)

( * ) Notice: Subject to any disclaimer, the term of this patent is extended or adjusted under 35 U.S.C. 154(b) by 0 days.

(21) Appl. No.: 10/334,411

(22) Filed: Dec. 30, 2002

(65) Prior Publication Data

US 2003/0153075 A1    Aug. 14, 2003

(30) Foreign Application Priority Data

Dec. 28, 2001    (KR)    ........................ 10-2001-0086765

(51) Int. Cl.
C07H 21/04    (2006.01)
C07H 21/00    (2006.01)
A61K 31/70    (2006.01)

(52) U.S. Cl. .................. 536/24.5; 514/44; 536/25.3

(58) Field of Classification Search ............... 536/24.5, 536/24.1, 23.1, 23.2, 24.3, 24.31; 435/91.1, 435/91.3, 6, 325, 375; 514/44
See application file for complete search history.

(56) References Cited

U.S. PATENT DOCUMENTS 5,683,874 A    11/1997    Kool
2002/0182586 A1 *    12/2002    Morris et al.    ............... 435/4

FOREIGN PATENT DOCUMENTS

| EP | 1239034 A2 | 9/2002 |
|---|---|---|
| WO | WO 00/61595 | * 10/2000 |
| WO | WO 00/61595 A1 | 10/2000 |

OTHER PUBLICATIONS

Han et al. Therapy with antisense TGF-B1 oligodeoxynucleotides reduces kidney weight and matrix mRNAs in diabetic mice. Apr. 2000. American Journal of Physiology-Renal Physiology. vol. 278. pp. F628-634.*
Spearman et al. Antisense oligodeoxyribonucleotide inhibition of TGF-B1 gene expression and alterations in the growth and mailgnant properties of mouse fibrosarcoma cells. 1994. Gene. vol. 149. pp. 25-29.*
Moon et al. Potent growth inhibition of leukemic cells by novel ribbon-type antisense oligonucleotides to c-myb1. Feb. 2000. Journal of Biological Chemistry. vol. 275. pp. 4647-4653.*
Fakhrai et al. Eradicatioin of established intracranial rat gliomas by transforming growth factor.beta. antisense gene therapy. Apr. 1996. Proceedings of the National Academy of Sciences, USA vol. 93 pp. 2909-2914.*

Moon et al., "Target site search and effective inhibition of leukaemic cell growth by a covalently closed multiple anti-sense oligonucleotide to c-myb", Biochem. J., 2000, 346: 295-303.
Futaki et al., "Arginine-rich Peptides", The Journal of Biological Chemistry, 2001, 276(8): 5836-40.
Efthymiadis et al., "The HIV-1 Tat Nuclear Localization Sequence Confers Novel Nuclear Import Properties", The Journal of Biological Chemistry, 1998, 273(3): 1623-8.
Wu et al., "TGF-Beta1 is an Autocrine-negative Growth Regulator of Human Colon Carcinoma FET Cells in vivo as Revealed by Transfection of an Anitsense Expression Vector", The Journal of Cell Biology, 1992, 116(1): 187-96.
Fitzpatrick et al., "Transforming Growth Factor-Beta:Antisense RNA-Mediated Inhibition Affects Anchorage-Independent Growth, Tumorigenicity and Tumor-Infiltrating T-Cells in Malignant Mesothelioma", Growth Factors, 1994, 11: 29-44.
Maggard et al., "Antisense TGF-Beta2 Immunotherapy for Hepatocellular Carcinoma: Treatment in a Rat Tumor Model", Annals of Surgical Oncology, 2001, 8(1): 32-7.
Akagi et al., "Inhibition of TGF-Beta1 expression by antisense oligonucleotides suppressed extracellular matrix accumulation in experimental glomerulonephritis," Kidney International, 50: 148-155 (1996).
Choi et al., "Prevention of tissue injury by ribbon antisense to TGF-Beta1 in the kidney," International Journal of Molecular Medicine, 15: 391-399 (2005).
Isaka, Y., "Application of gene therapy to kidney diseases," Clin Exp Nephrol, 3: 147-153 (1999).
Isaka et al., "Transforming growth factor-Beta1 antisense oligodeoxynucleotides block interstitial fibrosis in unilateral ureteral obstruction," Kidney International, 58: 1885-1892 (2000).
Ando et al., "Introduction of TGF-beta antisense oligodeoxynucleotides (ODN) into interstitial fibroblast blocked tubulointerstitial fibrosis in unilateral ureter obstruction (UUO) rats," Journal of Americal Society of Nephrology, 9: 512A (1998), abstract A2617.
Isaka Y et al., "Transforming growth factor-beta1 antisense oligodeoxynucleotides block interstitial fibrosis in unilateral ureteral obstruction," Kidney International, 58(5):1885-1892 (2000).
Isaka Y, "Application of gene therapy to kidney diseases," Clinical and Experimental Nephrology, 3:147-153 (1999).
Ando Y et al., "Introduction of TGF-beta antisense oligodeoxynucleotides (ODN) into interstitial fibroblast blocked tubulointerstitial fibrosis in unilateral ureter obstruction (UUO) rats," Journal of the American Society of Nephrology, 9: 512A (1998).
Akagi Y et al., "Inhibition of TGF-beta 1 expression by antisense oligonucleotides suppressed extracellular matrix accumulation in experimental glomerulonephritis," Kidney International 50(1) 148-155 (1996).
Moon et al., "Potent growth inhibition of leukemic cells by novel ribbon-type antisense oligonucleotides to c-myb1," The Journal of Biological Chemistry, 275(7): 4647-4653 (2000).
Moon et al., "Target site search and effective inhibition of leukaemic cell growth by a covalently closed multiple anti-sense oligonucleotide to c-myb," Biochem. J., 346:295-303 (2000).

* cited by examiner

*Primary Examiner*—Tracy Vivlemore
(74) *Attorney, Agent, or Firm*—Joseph Hyosuk Kim; JHK Law

(57) ABSTRACT

The present application describes a purified covalently closed antisense molecule, which specifically inhibits expression of TGF-β.

20 Claims, 8 Drawing Sheets

SEQUENCE LISTING

```
<160> NUMBER OF SEQ ID NOS: 5

<210> SEQ ID NO 1
<211> LENGTH: 58
<212> TYPE: DNA
<213> ORGANISM: Homo sapiens

<400> SEQUENCE: 1
gatccaggac tgtgtgtgat gtctttggtt ttgtcataga ttgcgttgtt gcggcctg        58

<210> SEQ ID NO 2
<211> LENGTH: 58
<212> TYPE: DNA
<213> ORGANISM: Artificial
<220> FEATURE:
<223> OTHER INFORMATION: Scramble sequence
<220> FEATURE:
<221> NAME/KEY: misc_structure
<222> LOCATION: (1)..(58)
<223> OTHER INFORMATION:

<400> SEQUENCE: 2
gatccgctgt cgtgctggtc ttgagttaat tcgttgttgt tgtctgagtt ggtatgcg        58

<210> SEQ ID NO 3
<211> LENGTH: 116
<212> TYPE: DNA
<213> ORGANISM: Artificial
<220> FEATURE:
<223> OTHER INFORMATION: ribbon-type antisense molecule specific for
      TGF-beta1

<400> SEQUENCE: 3
gatccaggac tgtgtgtgat gtctttggtt ttgtcataga ttgcgttgtt gcggcctgga      60
tccaggactg tgtgtgatgt ctttggtttt gtcatagatt gcgttgttgc ggcctg         116

<210> SEQ ID NO 4
```

-continued

```
<211> LENGTH: 13
<212> TYPE: PRT
<213> ORGANISM: Homo sapiens

<400> SEQUENCE: 4

Arg Lys Lys Arg Arg Gln Arg Arg Arg Pro Pro Gln Cys
1               5                   10

<210> SEQ ID NO 5
<211> LENGTH: 12
<212> TYPE: PRT
<213> ORGANISM: Homo sapiens

<400> SEQUENCE: 5

Arg Lys Lys Arg Arg Gln Arg Arg Pro Pro Gln
1               5                   10
```

TGF-β-SPECIFIC COVALENTLY CLOSED ANTISENSE MOLECULE

BACKGROUND OF THE INVENTION

This application claims the benefit of priority under 35 USC 119(a)-(d) to Republic of Korea application 10-2001-86765, filed Dec. 28, 2001.

1. Field of the Invention

The present invention relates to the field of biotechnology and especially antisense therapy using closed covalent antisense molecule that is targeted to TGF-β. The invention also relates to a method of delivering the antisense molecule to a cell. The invention further relates to a method of treating diseases caused by the production of TGF-β.

2. General Background and State of the Art

Renal tubulointerstitial fibrosis, characterized by the accumulation of extracellular matrix proteins (ECMs), is a common consequence of progressive renal diseases (Kuncio et al., Kidney Int. 39, 550-556(1991)). Obstructed kidney with unilateral ureteric obstruction (UUO) is a well established animal model system for renal injury accompanied by tubulointerstitial fibrosis (Klahr et al., Kidney Int. 54, 286-300(1998)). The mechanical disturbance resulting from ureteral ligation leads to hydronephrosis, loss of renal parenchyma, and tubular changes such as dilation, atrophy, and apoptosis (Gonzalez-Avila et al., Pathobiology 66, 196-204(1998); Truong et al., Kidney Int. 50, 200-207(1996)). Although the mechanisms underlying the progression of tubulointerstitial fibrosis have not been fully elucidated, numerous cytokines have been implicated as mediators of tubulointerstitial fibrosis in kidneys with UUO. Among these cytokines, transforming growth factor-β1 (TGF-β1) plays an important role in renal fibrosis, as evidenced by glomerulosclerosis and tubulointerstitial fibrosis (Schiffer et al., J. Clin. Invest. 108, 807-816 (2001); Wang et al., Kidney Int. 60, 96-105(2001)). TGF-β1 is involved in accumulation of ECMs responding to tissue injury for normal repair and is responsible for fibrotic changes by aberrant overproduction of ECMs such as proteoglycans, collagens, fibronectin, and glycoproteins (Branton et al., Microbes Infect. 1, 1349-1365(1999); Okuda et al., J. Clin. Invest. 86, 453-462(1990)). TGF-β1 also inhibits the degradation of newly synthesized matrix protein by upregulating the synthesis of protease inhibitors and downregulating the synthesis of matrix-degrading proteases. Thus, effective blockade of TGF-β1 synthesis or action appears to be a promising method for preventing fibrotic conditions as suggested by several reports (Border et al., Nature 360, 361-364(1992); Akagi et al., Kidney Int. 50, 148-155(1996); Isaka et al., Nat. Med. 2, 418-423(1996); Isaka et al., Kidney Int. 55, 465-475 (1999)).

Antisense oligonucleotides (AS oligos) have been valuable in the functional study of gene products by reducing expression of genes in a sequence-specific manner. However, the use of oligos still has several critical problems such as instability to nuclease, sequence nonspecificity and poor cellular uptake. Various chemically modified oligos such as phosphorothioate and methylphosphonate oligos have been developed to augment stability against nucleases. However, each of the modified oligonucleotides exhibits its own problems, which include lack of sequence specificity, insensitivity to RNaseH and prolongation of partial thrombosis time. Further, there has been fear that recycled hydrolyzed modified nucleotides may be incorporated into the genome during DNA repair and replication, causing mutations in genomic DNA. We previously reported that ribbon-type antisense (RiAS) oligos with a covalently closed structure were very stable and effective in specific ablation of target c-myb mRNA, and had few of the problems associated with other modified AS oligos (Moon et al., J. Biol. Chem. 275, 4647-4653(2000); and PCT/KR00/00305), which are incorporated by reference in their entirety.

U.S. Pat. No. 5,683,874 discloses forming a covalently closed type nucleic acid sequence but requires that a parallel and anti-parallel nucleic acid sequence be present on the opposite sides of the loop to form a triple helical structure. However, such structure is useful mainly for binding genomic promoter region and not for binding complementary mRNA for targeted degradation by RNase H. Thus, the '874 patent fails to disclose or suggest that a covalently closed antisense structure with or without such parallel and anti-parallel sequences may be effective in ablating target nucleic acid expression.

Cellular uptake of antisense oligos can be enhanced by forming complexes with liposomes. Although liposomes have several advantages such as low toxicity, lack of immunogenicity, and simplicity of production, liposomes exhibit relatively poor cellular uptake. It has been shown that a protein fused with the protein transduction domain of the tat polypeptide of human immunodeficiency virus (HIV) can be efficiently delivered to all tissues in mice, including the brain (Schwarze et al., Science 285, 1569-1572(1999)). The tat peptide covalently harnessed on the surface of liposomes increases intracellular delivery (Torchilin et al., Proc. Natl. Acad. Sci. USA 98, 8786-8791(2001)). Further, a small region of the tat protein, residues from 49 to 57 containing 2 lysines and 6 arginines, has nuclear localization property.

There is a continuing need to make therapeutic antisense molecules that are specific, safe and efficacious, as well as a system for delivering the antisense molecules effectively.

SUMMARY OF THE INVENTION

The present invention has met the above-described need.

In one aspect, the invention is directed to a RiAS molecule specifically targeted to TGF-β1 (TGF-β1 RiAS). In another aspect of the invention, TGF-β1 RiAS was designed and tested for its antisense activity for the prevention of fibrosis and tissue damage in the kidney. In yet another embodiment of the invention, the present is directed to an antisense molecule delivery mixture to improve cellular uptake. In particular, TGF-β1 RiAS was mixed with tat-like peptide, and then complexed with liposomes. The triple complex of TGF-β1 RiAS, tat or tat-like peptide and cationic liposomes was found to be effective in blocking TGF-β1 expression and in preserving tissue integrity in kidneys with UUO.

The present invention is directed to a purified covalently closed antisense molecule, which specifically inhibits expression of TGF-β. The covalently closed antisense molecule may have at least two loops separated by a stem structure, wherein at least one loop comprises a target antisense sequence to inhibit TGF-β expression. In particular, the TGF-β may be TGF-β1.

The covalently closed antisense molecule discussed above may comprise sequence that is substantially similar to SEQ ID NO:1.

The invention is also directed to a method of making the compound antisense compound discussed above, comprising ligating together at least two linear antisense molecules with stem-loop structure having either or both 5' or 3' ends be substantially complementary to each other so that a covalently closed antisense molecule is made. In this method, the linear antisense molecule may be specific for the same target nucleic acid or a different nucleic acid. In one aspect, although not limited by the length of the sequence, the complementary region may be about 1 to about 100 bases, 1-50 bases, 1-20 bases, and the like.

The invention is also directed to a method of inhibiting expression of TGF-β comprising contacting a sample comprising TGF-β expressing cells with the covalently closed antisense molecule described above.

The invention is further directed to a method of treating a condition caused by expression of TGF-β, comprising administering the covalently closed antisense molecule described above to a subject in need thereof. The condition may be without limitation, fibrosis, fibrosis in the kidney, tubulointerstitial fibrosis, fibrosis in the liver, or fibrosis in the lung.

The invention is directed to a method for treating unilateral ureteric obstruction comprising administering a composition comprising the covalently closed antisense molecule described above.

In invention is also directed to a method of preventing accumulation of extracellular matrix proteins at a site of injury comprising administering the covalently closed antisense molecule described above.

The invention is directed to a composition comprising a covalently closed antisense molecule, tat or tat-like peptide, and a carrier composition. The carrier may be a liposome, and the covalently closed antisense molecule may be targeted to TGF-β.

The invention is also directed to a method of delivering a covalently closed antisense molecule to a cell, comprising contacting the cell with a composition comprising covalently closed antisense molecule, a tat or tat-like peptide and a carrier composition. In an aspect of the invention, the tat or tat-like peptide and the carrier composition may be mixed before contacting the cell.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
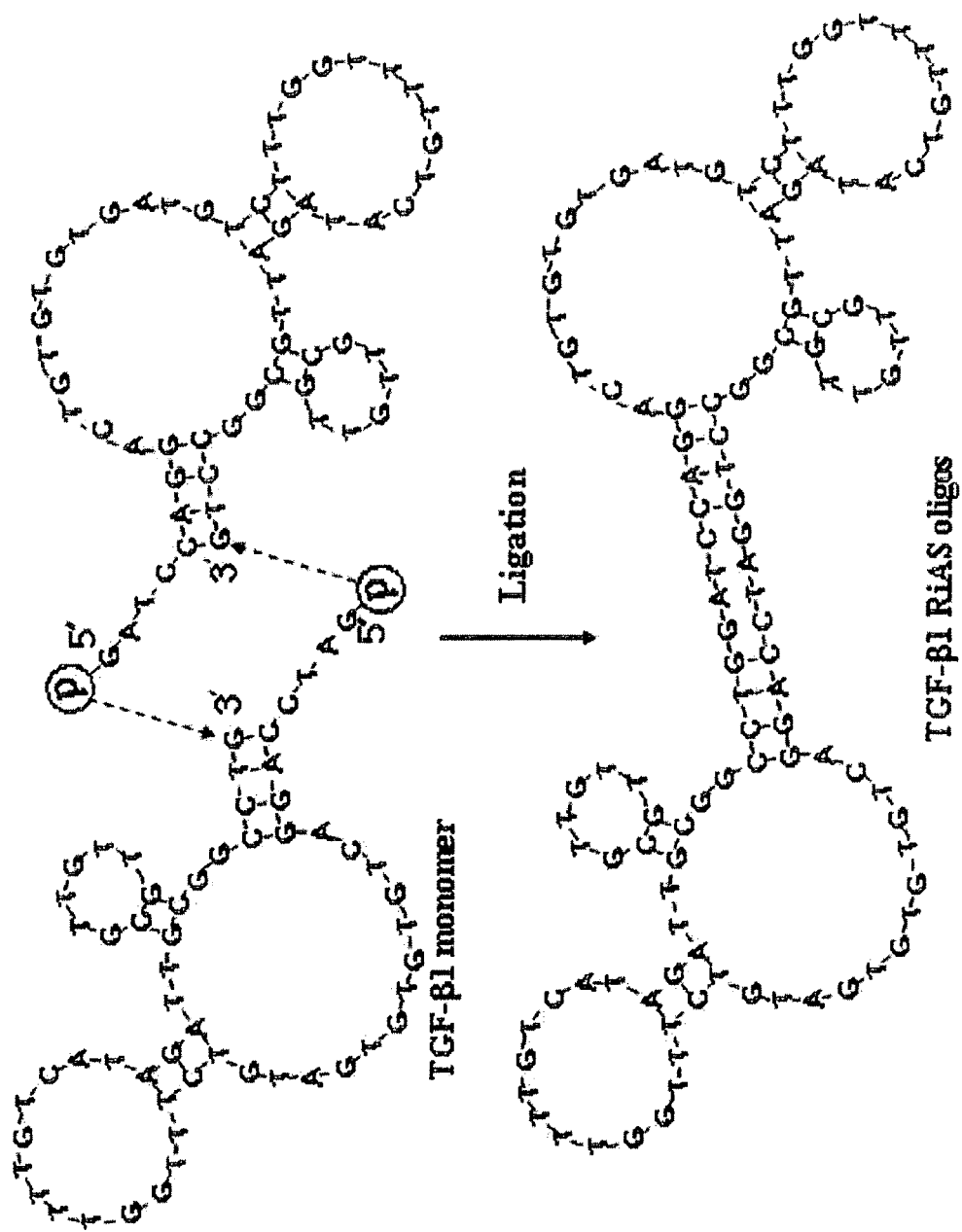
FIG. 1 shows schematic representation of ribbon-type antisense molecule to TGF-β1 (TGF-β1 RiAS), in particular, a 116-mer (SEQ ID NO:3). It is presumed that TGF-β1 monomeric oligos (SEQ ID NO:1) form a stem-loop structure. The stem is formed by complementary sequences at both ends of each oligo. The 5' terminus of the stem has 4 bases of a single-stranded overhang of 5'-GATC-3'. Two TGF-β1 monomer molecules were ligated to generate a covalently closed molecule with diad symmetry. RiAS oligos consist of two loops and an intervening stem. Each loop contains an antisense sequence to TGF-β1.

In the present application, "a" and "an" are used to refer to both single and a plurality of objects.

As used herein, the term "antisense" or "AS" means antisense nucleic acid (DNA or RNA) and analogs thereof and refers to a range of chemical species having a range of nucleotide base sequences that recognize polynucleotide target sequences or sequence portions through hydrogen bonding interactions with the nucleotide bases of the target sequences. The target sequences may be single- or double-stranded RNA, or single- or double-stranded DNA.

Such RNA or DNA analogs comprise but are not limited to 2'-O-alkyl sugar modifications, methylphosphonate, phosphorothioate, phosphorodithioate, formacetal, 3'-thioformacetal, sulfone, sulfamate, and nitroxide backbone modifications, amides, and analogs wherein the base moieties have been modified. In addition, analogs of molecules may be polymers in which the sugar moiety has been modified or replaced by another suitable moiety, resulting in polymers which include, but are not limited to, morpholino analogs and peptide nucleic acid (PNA) analogs. Such analogs include various combinations of the above-mentioned modifications involving linkage groups and/or structural modifications of the sugar or base for the purpose of improving RNaseH-mediated destruction of the targeted RNA, binding affinity, nuclease resistance, and or target specificity.

As used herein, "antisense therapy" is a generic term, which includes specific binding of the covalently closed antisense nucleic acid molecules that include an antisense segment for a target gene to inactivate or ablate target RNA sequences in vitro or in vivo.

As used herein, "cell proliferation" refers to cell division. The term "growth," as used herein, encompasses both increased cell numbers due to faster cell division and due to slower rates of apoptosis, i.e. cell death. Uncontrolled cell proliferation is a marker for a cancerous or abnormal cell type. Normal, non-cancerous cells divide regularly, at a frequency characteristic for the particular type of cell. For instance, when a cell has been transformed into a cancerous state, the cell divides and proliferates uncontrollably. Also, after injury, extracellular cell matrix is overgrown. Inhibition of proliferation or growth modulates the uncontrolled division of the cell or the formation of dense tissue.

As used herein, "fibrosis" refers to the creation of dense, firm scar tissue in response to previous tissue damage or disease.

As used herein, a "gene" refers to either the complete nucleotide sequence of the gene, or to a sequence portion of the gene.

As used herein, the terms "inhibiting" and "reducing" are used interchangeably to indicate lowering of gene expression or cell proliferation or tissue growth or any other phenotypic characteristic.

As used herein, "substantially complementary" means an antisense sequence having about 70%, 75%, 80%, 85%, 90%, 95%, 96%, 97%, 98%, or 99% homology with an antisense compound which itself is complementary to and specifically binds to the target RNA. As a general matter, absolute complementarity may not be required. Any antisense molecule having sufficient complementarity to form a stable duplex or triplex with the target nucleic acid is considered to be suitable. Since stable duplex formation depends on the sequence and length of the hybridizing antisense molecule and the degree of complementarity between the antisense molecule and the target sequence, the system can tolerate less fidelity in complementarity with larger than conventionally used short linear oligonucleotides of from about 13 to about 30 bases.

As used herein, "substantially similar" means a nucleic acid sequence having about 70%, 75%, 80%, 85%, 90%, 95%, 96%, 97%, 98%, or 99% homology with another nucleic acid. For an antisense molecule having a substantially similar sequence to another antisense molecule directed to the same target, it is the functional capability of the substantially similar molecule that is important, so long as the substantially similar molecule shows target inhibiting activity.

While formation of triplex structure may be within the purview of the present invention, it is understood that such formation is not necessary to practice and obtain the advantageous features of the present invention. For example, it is not necessary to design an oligonucleotide loop structure with parallel and anti-parallel sequences on opposite sides of the loop as disclosed in U.S. Pat. No. 5,683,874.

As used herein, "target" or "targeting" refers to a particular individual gene for which an antisense molecule is made. In certain contexts, "targeting" means binding or causing to be bound the antisense molecule to the endogenously expressed transcript so that target gene expression is eliminated. The target nucleotide sequence may be selected from genes involved in various malignancies, including genes involved in the initiation and progression of various diseases such as immune diseases, infectious diseases, metabolic diseases and hereditary diseases, fibrotic disorder or any other disease caused by abnormal expression of genes, including genes belonging to TGF-β superfamily, and in particular, TGF-β1.

The antisense molecule of the invention was found to be superior to conventional linear synthetic AS-oligos in biochemical and biologic activities. While conventional AS-oligos can be easily synthesized by a DNA synthesizer, they require the selection of a target site. The process of selecting for the target site is sometimes termed 'AS-oligo design'. This process is time consuming and often inconclusive. In addition, synthesized AS-oligos are unstable to nucleases, have frequent sequence errors, entail high production cost, and exhibit poor cellular uptake even after complexation with liposomes.

As used herein, "tat peptide" and "tat-like peptide" are related terms. In particular, tat peptide refers to a portion of the tat protein with possible modifications. Tat-like peptide refers to a peptide that facilitates insertion of nucleic acids into the cell in a similar manner as tat peptide. In one aspect, tat-like peptide may share sequence similarity, in other aspects, the tat peptide may share tertiary or charge similarity with tat peptide, so long as transport of the antisense compound of the invention is facilitated into the cell. Throughout the application, where tat peptide is mentioned as facilitating transport of the antisense molecule into a cell, it can be assumed that tat-like peptide may also be used.

TGF-β1

TGF-β1 is a 25 kDa homodimer composed of two 12.5 kDa subunits held together by disulfide bonds. TGF-β1 was originally defined by its ability to cause the phenotypic transformation of rat fibroblasts. TGF-β1 is a multipotent cytokine with cell- and dose-dependent activities. Although TGF-β1 is a growth inhibitor for most cell types, it can act as a stimulator for some cell types. TGF-β1 has ubiquitous distribution. For reviews on TGF-β1, see Massagué, *J. Ann. Rev. Cell Biol.* 6, 597. (1990); Letterio et al., *Ann. Rev. Immunol.* 16, 137 (1998). TGF-β1 demonstrates regulatory effects on a wide range of cell types, and modulates embryonic development, bone formation, mammary development, wound healing, haematopoiesis, angiogenesis, cell cycle progression and the production of the extracellular matrix. With respect to the immune system, TGF-β1 inhibits T and B cell proliferation and acts as an anti-inflammatory molecule both in vitro and in vivo. TGF-β1 inhibits macrophage maturation and activation, and also inhibits the activity of natural killer cells and lymphokine-activated killer (LAK) cells and blocks cytokine production.

Virtually all cells have TGF-β1 receptors, which control a variety of functions in these cells. Nine membrane proteins that bind TGF-β have been identified to date (reviewed in 8). The most widely distributed of these are TGF-β receptors I and II, proteins with molecular weights of 53 kDa and 70 kDa, respectively. Loss of the Type I and/or Type II receptor correlates with the loss of cellular responsiveness to TGF-β. The Type II receptor has been cloned and has been shown to contain a functional serine/threonine kinase domain. TGF-β1 is produced in vivo in an inactive, latent form composed of the mature 25 kDa dimer, which is noncovalently associated with its 75 kDa propeptide dimer (a latency-associated propeptide). TGF-β1 is species cross-reactive with murine, bovine, porcine and rhesus monkey cells.

Transforming Growth Factor-β (TGF-β) Superfamily

Transforming growth factor-β superfamily encompasses a group of structurally related proteins, which affect a wide range of differentiation processes during embryonic development. The family includes without limitation Müllerian inhibiting substance (MIS), which is required for normal male sex development (Behringer et al., Nature, 345:167, 1990), Drosophila decapentaplegic (DPP) gene product, which is required for dorsal-ventral axis formation and morphogenesis of the imaginal disks (Padgett et al., Nature, 325: 81-84, 1987), the Xenopus Vg-1 gene product, which localizes to the vegetal pole. of eggs (Weeks et al., Cell, 51:861-867, 1987), the activins (Mason, et al., Biochem, Biophys. Res. Commun., 135:957-964, 1986), which can induce the formation of mesoderm and anterior structures in Xenopus embryos (Thomsen et al., Cell, 63:485, 1990), and the bone morphogenetic proteins (BMP's, such as BMP-2, 3, 4, 5, 6, 7 and 8, osteogenin, OP-1) which can induce de novo cartilage and bone formation (Sampath, et al., J. Biol. Chem., 265: 13198, 1990). The TGF-β gene products can influence a variety of differentiation processes, including adipogenesis, myogenesis, chondrogenesis, hematopoiesis, and epithelial cell differentiation (for a review, see Massague, Cell 49:437, 1987), which is incorporated herein by reference in its entirety.

The proteins of the TGF-β superfamily are initially synthesized as a large precursor protein, which subsequently undergoes proteolytic cleavage at a cluster of basic residues approximately 110-140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species have been found to be biologically active, but for other family members, like the inhibins (Ung et al., Nature, 321:779, 1986) and the TGF-β's (Cheifetz et al., Cell, 48:409, 1987), heterodimers have also been detected, and these appear to have different biological properties than the respective homodimers.

Members of the superfamily of TGF-β genes include without limitation TGF-β3, TGF-β2, TGF-β4 (chicken), TGF-β1, TGF-β5 (Xenopus), BMP-2, BMP-4, Drosophila DPP, BMP-5, BMP-6, Vgrl, OP-1/BMP-7, Drosophila 60A, GDF-1, Xenopus Vgf, BMP-3, Inhibin-βA, Inhibin-βB, Inhibin-α, and MIS. These genes are discussed in Massague, Ann. Rev. Biochem. 67:753-791, 1998, which is incorporated herein by reference in its entirety.

Preferably, the member of the superfamily of TGF-β proteins is TGF-β. More preferably, the member is TGF-β1, TGF-β2, TGF-β3, BMP-2, BMP-3, BMP-4, BMP-5, BMP-6, BMP-7, or BMP-8. Even more preferably, the member is human or porcine TGF-β. Still more preferably, the member is human or porcine TGF-β1, TGF-β2, or TGF-β3. Most preferably, the member is human or porcine TGF-β1.

Covalently Closed Antisense Oligo

Conventional wisdom in the field of antisense therapy has discouraged using long antisense molecules because it was thought that longer AS-oligos tend to be less specific, harder to synthesize and inefficient in cellular uptake. Indeed, chemically modified second generation AS-oligos such as phosphorothioate modified oligos, have reduced sequence specificity as the length of the AS-oligos is extended. Furthermore, synthesis of linear AS-oligos becomes increasingly difficult, and sequence fidelity declines markedly as the length of AS-oligos increases. On the other hand, closed covalent antisense oligonucleotide molecules have shown greater stability even though the molecules are longer and contains additional target sites as compared with short linear oligonucleotides.

The RiAS oligo of the invention may be made by ligating together at least two linear oligonucleotides possessing antisense sequence that targets the same or different gene, or multiple targets within a single linear oligonucleotide. The ligation may be made at the ends, preferably at the 5' ends which are phosphorylated, where a few bases at the 5' end are substantially complementary to each other so that hybridization and ligation occur resulting in the formation of a ribbon-type oligonucleoide. The length of the molecule is not limited and in particular may be from about 20 to about 1000 nucleotides, about 20 to 700 nucleotides, about 20 to 600 nucleotides, about 20 to 500 nucleotides, about 20 to 400 nucleotides, about 20 to about 300 nucleotides, preferably about 20 to about 150 nucleotides, or more preferably about 20 to about 120 nucleotides.

In a specific embodiment of the present invention, ribbon-type antisense to TGF-β1 mRNA was shown to eliminate the target mRNA in a sequence-specific manner and to alleviate global tissue injury in kidneys with UUO. The results of this study indicates that TGF-β1 RiAS oligos may be used as a therapeutic agent for various renal diseases in connection with either tissue fibrosis or UUO conditions. The results in this study demonstrate enhanced properties of the ribbon-type antisense molecule. Efficient delivery of TGF-β1 RiAS into tubular epithelial cells can effectively suppress tubular TGF-β1 expression, and thereby block consequent tubular lesions including atrophy, dilation, and apoptosis in the kidney with UUO.

Tat and Tat-Like Peptide

In general, antisense oligos show poor cellular uptake due to anionic charges on their polymeric backbone. Cellular uptake of oligonucleotides can be significantly improved when complexed with liposomes (Wheeler et al., Proc. Natl. Acad. Sci. USA 93, 11454-11459(1996)). However, nonviral delivery vehicles including liposomes do not provide uptake efficiency that is satisfactory for many types of cells, especially cells of primary culture. Thus, developing an improved transfection reagent would be beneficial for use in both in vitro cell-line studies and in vivo applications. We devised a simple mixture system comprising antisense oligos, tat-like polypeptide, and liposomes or any other carrier to enhance cellular uptake of RiAS oligos. A short fragment of the tat protein has been shown to have properties of nucleic acid condensation, membrane penetration, and nuclear localization. These properties may be of use in enhancing cellular uptake of nucleotide molecules as well as conjugated proteins (Efthymiadis et al., J. Biol. Chem. 273, 1623-1628(1998); Schwartz et al., Curr. Opin. Mol. Ther. 2, 162-167(2000)). The tat peptide was found to be more effective than comparable short peptides with similar properties such as SV 40 large T antigen peptide (Data to be reported elsewhere).

The specifically exemplified tat peptide in the present application has the amino acid sequence: RKKRRQRRRP-PQC (SEQ ID NO:4). However, it is understood that other sequences are included within the purview of the tat peptide of the invention. For instance, RKKRRQRRRPPQ (SEQ ID NO:5) (49-59 of tat protein), may be used. In addition, about 86 amino acid tat proteins may also be used. Modifications to the tat peptide is permissible, such as but not limited to carboxyl group modification of RKKRRQRRRPPQ (e.g.: tat-RGD). Moreover, other sequences may be used as well, such as the first exon (48-72 amino acid) portion of the tat protein.

In another aspect of the invention, other tat-like peptides may be used, such as without limitation, Antp, W/R, NLS, AlkCWK16, DiCWK18, Transportan, K16RGD, VP22, SCWKn, (LARL)n, HA2, RGD, L oligomer, SV40, and the like, so long as the peptides facilitate the insertion of the antisense compound into the cell.

In one embodiment of the invention, the carrier may be covalently linked to the tat or tat-like protein or any other carrier peptide, and may be otherwise complexed or mixed with the tat or tat-like protein or any other carrier peptide that may be used.

TGF-β1 Related Diseases

The invention is directed to treating or preventing any disorder, which is caused by the expression of TGF-β1 or any disorder in which cessation of TGF-β1 expression at the locus would be beneficial and results in treatment or alleviation of symptoms of the disease. Such diseases may include without limitation, skin lesions such as scleroderma, bone marrow fibrosis such as myeloproliferative disorders, renal fibrosis, hepatic fibrosis, lung fibrosis, chemotherapy/radiation induced fibrosis, stenosis, transplantation (allograft rejection), peyronies's disease, chronic pancreatitis, vascular disease, liver cirrhosis (alcohol, HCV), asthma, emphysema, bowel disease, Crohn's disease, Gaucher's disease, vascular disease, cardiac fibrosis, systemic sclerosis and the like.

Glomerulosclerosis and Fibrosis

Major production sources of TGF-β1 in the kidney with UUO are interstitial fibroblasts and tubular epithelial cells (Isaka et al., *Kidney Int.* 58, 1885-1892(2000)). We detected a fluorescent signal in tubular epithelial cells when the oligo complex was infused through the ureter. It was previously reported that retrograde infusion of antisense oligos via the ureter using HVJ liposomes led to selective transfection of interstitial fibroblasts (Tsujie et al., *Kidney Int.* 57, 1973-1980 (2000)). In another report, when SV40 large T antigen gene complexed with HVJ/liposomes was introduced into the kidney through the renal artery using a cannula, gene expression was detected in glomerular cells (Tomita et al., *Biochem. Biophys. Res. Commun.* 15, 129-134(1992)). Three different routes, including intra-renal pelvic retrograde, parenchymal injection and renal arterial injection were studied for liposome (DOTMA/DOPE)-mediated gene delivery (Lai et al., *Gene Ther.* 4, 426-431(1997)). β-galactosidase activity was detected in cortical and outer medullary cells by pelvic retrograde and renal arterial injections, but not by parenchymal injection. Our observations and those of others demonstrate that both delivery routes and vector tropisms are important factors in determining the target cell type in the kidney.

In the present study, treatment with TGF-β1 RiAS significantly decreased TGF-β1 expression and tubular apoptosis in the kidney, consequently ameliorating global tissue injury. Since tissue fibrosis is a critical aspect in the progression of many types of human diseases occurring in the kidney, liver and lung, it is contemplated that fibrotic lesions in these organs are treated by administering ribbon-type antisense oligos to TGF-β1 in these other conditions.

Unilateral Ureteric Obstruction (UUO)

UUO is a clinical condition that can arise from a number of congenital or acquired disease processes. It is associated with a marked decrease in function of the obstructed kidney (Klahr, S. *Kidney Int.* 54, 286-300(1998)). The identification of factors that mediate tubular damage may be of value in preservation and recoverability of injured kidneys. Kidneys with UUO caused by mechanical obstruction overproduces profibrotic and proapoptotic mediators, especially TGF-β1 (Kaneto et al., *Kidney Int.* 44, 313-321(1993)). It has been reported that TGF-β1 is predominantly expressed in renal tubular cells in the cortex and outer medulla but is also expressed in peritubular interstitial cells (Fukuda et al., *Am. J. Physiol. Renal Physiol.* 281, F513-F521(2001)). TGF-β is also involved in apoptosis of tubular cells exposed to mechanical stretch (Miyajima et al., *Kidney Int.* 58, 2301-2313(2000)).

Therapeutic Composition

In one embodiment, the present invention relates to treatment for various diseases that are characterized by excessive formation of extracellular matrix, such as fibrosis or any other disease in which a member of the TGF-β superfamily is normally or abnormally expressed, where inhibition of expression of the gene is desired. In this way, the inventive therapeutic compound may be administered to human patients who are either suffering from or prone to suffer from the disease by providing compounds that inhibit the expression of a member belonging to the TGF-β superfamily. In particular, the disease is associated with fibrosis in the kidney, liver and lung, among others.

The formulation of therapeutic compounds is generally known in the art and reference can conveniently be made to Remington's Pharmaceutical Sciences, 17th ed., Mack Publishing Co., Easton, Pa., USA. For example, from about 0.05 μg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitized in vitro and adoptively transferred to the recipient). Depending on the route of administration, the peptide may be required to be coated in a material to protect it from the action of enzymes, acids and other natural conditions which may inactivate the ingredients.

For example, the low lipophilicity of the antisense molecules will allow them to be destroyed in the gastrointestinal tract by enzymes capable of cleaving peptide bonds and in the stomach by acid hydrolysis. In order to administer the antisense molecules by other than parenteral administration, they will be coated by, or administered with, a material to prevent its inactivation. For example, antisense molecules may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the antisense molecules are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

Covalently Closed Antisense Molecule Delivery Carriers

The antisense delivery carrier of the invention may include a variety of chemical compounds or methods that facilitate the delivery of the antisense compounds of the invention into the cell of interest. A nucleic acid delivery method or carrier used in the invention may include and is not limited to cationic liposomes, PEG-lipid, PEG, poly-L-lysine, poly-D-lysine, dendrimer, Poly (D,L-lactic acid), virosomes, electroporation, magnetofection, naked DNA, lipid-polycation-DNA (LPD), folate-conjugated nanometric particles, cationic nanoparticle (NP) coupled to an integrin alphavbeta3-targeting ligand, (modified) virus coupled with DNA, short amphipathic peptide, a gene-activated matrix (GAM), poly(alpha-(4-aminobutyl)-L-glycolic acid) (PAGA), imidazole-containing polymers, chitosan, gelatin, atelocollagen, poly ((D), (L)-lactic-co-glycolic acid) (PLGA), cyclodextrin based polymers, histidine and lysine (HK) polymer, glyco-targeted delivery systems, porous polymer microspheres, and the like.

Various delivery systems are known and can be used to administer a compound of the invention, e.g., encapsulation in liposomes, microparticles, microcapsules, recombinant cells capable of expressing the antisense compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical antisense compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Cell Line and Animals

Rat hepatoma cell line, H4-IIE was obtained from American Type Culture Collection and maintained in EMEM medium containing 10% heat-inactivated fetal bovine serum (JBI, Daegu, Korea) and penicillin (100 U/ml)/streptomycin (100 µg/ml) in a humidified 5% $CO_2$ incubator at 37° C.

Male Sprague-Dawley (SD) rats were supplied from SLC (Hamamatsu, Shizuoka, Japan). Animals were housed in groups of 6 with free access to standard chow and water. Male SD rats, weighing 200-250 g, were used in these experiments. After anesthesia by the intraperitoneal injection of pentobarbital (5 mg/100 g body weight), the left kidney was exposed via an abdominal midline incision. Rats were subjected to ureteral ligation proximal to the left kidney, which was followed by a retrograde injection of TGF-β1 RiAS or control oligos using a 24-gauge catheter syringe.

Example 2

Construction of Rat TGF-β1 RiAS

Oligos were synthesized using an automated DNA synthesizer Expedite™8909 (Applied Biosystems, Foster City, Calif.). Target sites for AS oligos were selected by sequential overlapping simulation of secondary structures using the DNAsis program (Hitachi Software, San Bruno, Calif.) (Matsuda et al., *Mol. Biol. Cell* 7, 1095-1106(1996)). Antisense sequences to TGF-β1 and sequences of scrambled oligos are as follows: antisense sequence: 5'-GAT CCA GGA CTG TGT GTG ATG TCT TTG GTT TTG TCA TAG ATT GCG TTG TTG CGG CCT G-3' (SEQ ID NO:1), and scrambled sequence: 5'-GAT CCG CTG TCG TGC TGG TCT TGA GTT AAT TCG TTG TTG TTG TCT GAG TTG GTA TGC G-3' (SEQ ID NO:2). See Table 1.

TABLE 1

Sequence of ribbon-type antisense oligos derived from TGF-β1 sequence.

| | Complementary site in TGF-β1 sequence | Size (mer) | Antisense sequence* |
|---|---|---|---|
| TGF-β1 RiAS | 757-802 | 58 | GATCCAGGACTGTGTGTGATGTCTTTGG TTTTGTCATAGATTGCGTTGTTGCGGCC TG (SEQ ID NO:1) |
| Scrambled RiAS | Non-specific | 58 | GATCCGCTGTCGTGCTGGTCTTGAGTTA ATTCGTTGTTGTTGTCTGAGTTGGTATG CG (SEQ ID NO:2) |

*The target site search for TGF-β1 RiAS oligos was employed to find regions of TGF-β1 sequence that are free of secondary structures. Simulation of secondary structures was performed in a sequential and overlapping manner.

It is assumed that both TGF-β1 antisense and scrambled oligos form stem-loop structures. The stem is formed by complementary sequences at both ends of each oligo. The 5' terminus of the stem has 4 bases of a single-stranded sequence of 5'-GATC-3'. Two TGF-β1 antisense oligomer having stem-loop structure were ligated to form a ribbon-type antisense molecule by the presence of four complementary base sequences at 5' ends of the molecules. One unit of T4 DNA ligase (Takara Shuzo, Kyoto, Japan) was added to generate a covalently ligated molecule with diad symmetry. Accordingly, TGF-β1 RiAS consists of two loops and one intervening stem. Each loop contains TGF-β1 antisense sequences. RiAS oligos were electrophoresed on a 15% denaturing polyacrylamide gel and examined for their resistance to exonuclease III and for retardation on an acrylamide gel. Two scrambled oligos were also covalently combined to form a ribbon-type control oligo, which is denoted SC RiAS for convenience.

Example 3

Transfection of RiAS by Liposome/Tat Peptide Complex

Four micrograms of DOTAP/DOPE (Avanti, Alabaster, Ala.) in 100 μl Opti-MEM (GibcoBRL, Rockville, Md.) were added to a tube containing Opti-MEM suspension, tat peptide and the antisense oligos. The mixture was incubated for 10 min. Ten thousand cells in each well of a 96-well plate were treated with the triple complex of oligos-tat-liposomes in 100 μl volume. Antisense oligos were used in the amount of either 0.1 or 0.3 μg. H4-IIE cells were incubated in a 5% $CO_2$ incubator at 37° C. for 5 hr. Cells were then added with 100 μl of Opti-MEM with 20% FBS, and further incubated at 37° C. for 16 h before assay.

Example 4

Isolation of RNA and Reverse Transcriptase Polymerase Chain Reaction (RT-PCR)

Total RNA was isolated with Tripure™ Isolation Reagent (Roche, Indianapolis, Ind.). Cells were harvested and added with 0.4 ml of Tripure reagent, 10 μl of glycogen (1 mg/ml), and 80 μl of chloroform to obtain total RNA. RT-PCR was performed in a single reaction tube with Access™ RT-PCR kit (Promega, Madison, Wis.). RNA, PCR primers, avian myeloblast virus (AMV) reverse transcriptase (5 units/μl), Tfl DNA polymerase (5 units/μl), dNTP (10 mM, 1 μl), and $MgSO_4$ (25 mM, 2.5 μl) were added to a PCR tube, and water was added to adjust to a final volume of 50 μl. cDNA was synthesized for 45 min at 48° C., and was amplified through 30 amplification cycles (94° C. for 30 s, 56° C. for 1 min, 68° C. for 2 min) in a DNA thermal cycler (MJ Research, Watertown, Mass.). Amplified PCR product was confirmed on a 1.5% agarose gel, and quantification was done with a gel documentation program (Bio-Rad, Hercules, Calif.). PCR products were transferred to a nitrocellulose membrane and hybridized with internal oligonucleotides labeled with Fluorescein-11-dUTP (Amersham, Arlington Heights, Ill.). The signal was detected using an ECL detection kit.

Example 5

FITC-Oligonucleotide Delivery into the Kidney

Linear oligos were labeled with fluorescein using Labe-IIT™ fluorescein nucleic acid labeling kit (Mirus, Madison, Wis.) according to the manufacturer's recommendations. The mixture containing the complex of oligos labeled with FITC, tat polypeptide, and DOTAP/DOPE was infused to the left kidney through the ureter. The kidney was removed after 24 hr, and was embedded in a Tissue-Tek™ OCT compound (Miles, Elkhart, Ill.) under liquid nitrogen. Tissue blocks of the perfusion-fixed kidney were cryosectioned to 10 μm thickness and mounted on Poly-Prep™ slides (Sigma, St. Louise, Mo.). The tissues were mounted with Synthetic Mountant™ (Shandon, Pittsburgh, Pa.) for microscopic observations. The efficacy of gene transfer was evaluated using a fluorescent microscope with frozen sections of the kidney.

Example 6

TUNEL Assay to Detect Apoptosis

To detect fragmented DNA in the cells of kidneys with UUO, a TUNEL assay was performed using an in situ cell death detection kit (Roche) with minor modifications. Slides were deparaffinized and quenched for endogenous peroxidase activity for 30 min with 0.3% $H_2O_2$ in methanol. The slides were boiled in 10 mM citrate buffer for 10 min, rinsed with PBS, and incubated with deoxynucleotidyl transferase (TdT) with fluorescein-dUTP for 1 hr. The reaction was stopped with a terminating buffer. Then the slides were washed with PBS and were incubated with alkaline phosphatase conjugated with anti-fluorescein antibody at room temperature for 30 min. After washing to remove unbound enzyme conjugate, slides were developed with NBT/BCIP (Sigma) for 1 to 5 min. Positive renal tubular cells were counted in high-power microscopic fields (400×).

Example 7

Immunostaining for TGF-β1

Cryostat sections were sequentially incubated with Bouin's fixative at 4° C. for 5 min, acetone at −20° C. for 10 min, methanol for 15 min, 2% paraformaldehyde for 2 min, 4% paraformaldehyde for 4 min and 70% ethanol for 10 min, and were then rehydrated with graded ethanol. The tissue sections were washed with PBS and incubated with methanol containing 0.3% $H_2O_2$ for 30 min to remove endogenous peroxidase activity. Blocking was performed in PBS containing 10% FBS for 1 hr, and the tissue sections were incubated with anti TGF-β1 antibody (Santa Cruz Biotechnology, Santa Cruz, Calif.) in PBS containing 0.5% BSA and 2% FCS at 4° C. overnight. The next day, the tissue sections were incubated with anti-rabbit HRP conjugates (Sigma) at room temperature for 1 hr. The tissue section was incubated with Diamine benzidine (Sigma) for 5 min, dehydrated with ethanol, and mounted with Synthetic Mountant™ before microscopic observations.

Example 8

Statistical Analysis

Results are expressed as means ± standard deviation (SD). Statistical significance was determined using Student's t test. $P<0.05$ was considered significant.

Example 9

Results

Example 9.1

Construction of Stable RiAS Oligos for TGF-β1

Messenger RNA forms secondary or tertiary structures in cell cytoplasm. These structural complexities of mRNA arise from base pairing among its own bases and from binding with RNA binding proteins. For this reason, selection of an effective target site has been considered an important process in designing antisense oligos. We have previously shown that secondary structure simulation in a sequential and overlapping manner can be effectively utilized to find antisense target sequences along target mRNA (Moon et al., *J. Biol. Chem.* 275, 4647-4653(2000); Matsuda et al., *Mol. Biol. Cell* 7, 1095-1106 (1996)). The entire length of TGF-β1 mRNA was examined in an effort to find an antisense target site that was readily accessible to an antisense molecule.

Figure 2:
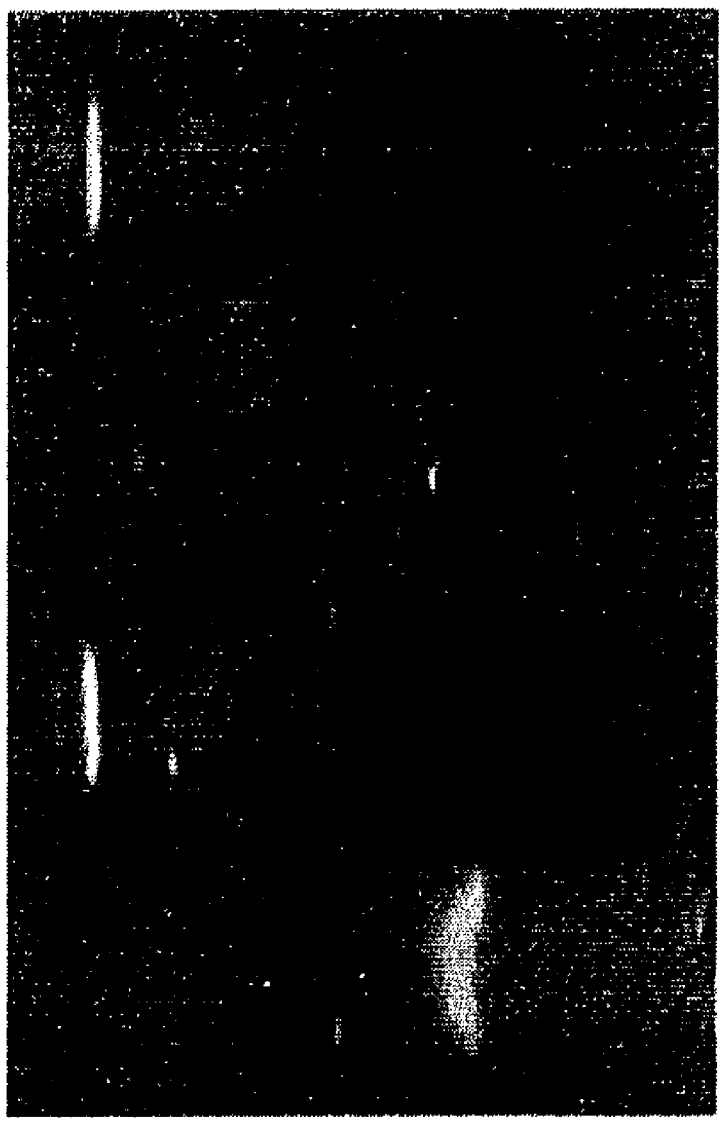
FIG. 2 shows resistance of TGF-β1 RiAS oligos to exonuclease III. Oligos were analyzed on a 15% denaturing polyacrylamide gel. Lane 1; 58 mer TGF-β1 AS oligos, lane 2; 116 mer TGF-β1 RiAS, lane 3; 58 mer TGF-β1 AS oligos treated with exonuclease III, lane 4; 116 mer TGF-β1 RiAS treated with exonuclease III.
Figure 4:
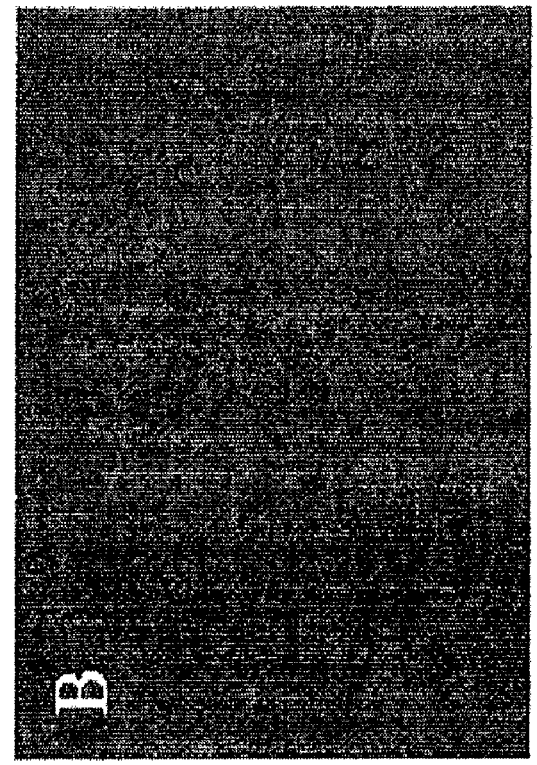
FIGS. 4A-4B show delivery of antisense oligos into the kidney through the ureter. The antisense oligos labeled with FITC at the 3' end were infused to the left kidney through the ureter after ureteral ligation. Perfusion-fixed kidney tissue blocks were cryosectioned, and the tissues were mounted with synthetic mountant for microscopic observation (magnification, 250X). A, FITC-oligos complexed with tat peptide and liposome; B, FITC-oligos alone.
Figure 4:
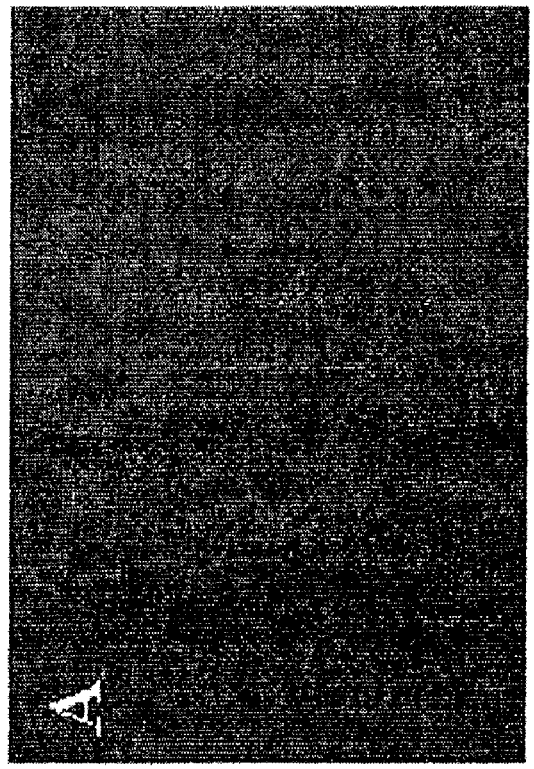

The TGF-β1 specific antisense oligo forms a stem-loop structure with an overhanging sequence of GATC at the 5' terminus. Two identical AS oligos were covalently ligated to form a ribbon-type antisense molecule termed TGF-β1 RiAS (FIG. 1). As expected, the dimeric TGF-β1 RiAS oligo was shown to be retarded on denaturing polyacrylamide gel when compared with the monomeric linear precursor (FIG. 2). The RiAS oligos were resistant to exonuclease III and were observed as a major band (116 mer) on polyacrylamide gel (lane 4). By contrast, the linear precursor of TGF-β1 RiAS was completely degraded by exonuclease III in 2 hr (lane 3). These results demonstrate that TGF-β1 RiAS molecules have a ribbon-type closed structure, without an open end that can be attacked by exonucleases.

antisense treatment, and were examined for cellular uptake. When the antisense oligos were complexed with the tat peptide and liposomes, a strong fluorescent signal was observed in tubular epithelial cells (FIG. 4A). However, fluorescent signals were not detected in tissues when antisense oligos alone were used without carrier liposomes (FIG. 4B). Control kidneys with sham treatment were shown to have no fluorescent signal.

Example 9.4

Significant Alleviation of Tissue Damage by TGF-β1 RiAS

After observing effective elimination of TGF-β1 mRNA in vitro and efficient tissue uptake of the FITC labeled antisense oligos in vivo, TGF-β1 RiAS was tested for its efficacy in preventing renal injury in an animal model. Unilateral ureteric obstruction (UUO) results in rapid renal injury, and the kidney with UUO is an established animal model system with clinical relevance.

TABLE 2

Weight ratio change (kidneys weight per body weight) of the left kidney with UUO after treatment with TGF-β1 RiAS.

| | Groups | | | | |
|---|---|---|---|---|---|
| | Naive | UUO only | UUO + PBS | UUO + SC-RiAS | UUO + TGF-β1 RiAS |
| Left | 0.46 ± 0.03% | 0.99 ± 0.10% | 0.95 ± 0.08% | 1.07 ± 0.12% | 0.68 ± 0.09%[#] |
| Right | 0.42 ± 0.03% | 0.47 ± 0.04% | 0.45 ± 0.06% | 0.40 ± 0.02% | 0.46 ± 0.08% |

Example 9.2

Specific Reduction of TGF-β1 mRNA in vitro by TGF-β1 RiAS

Figure 3:
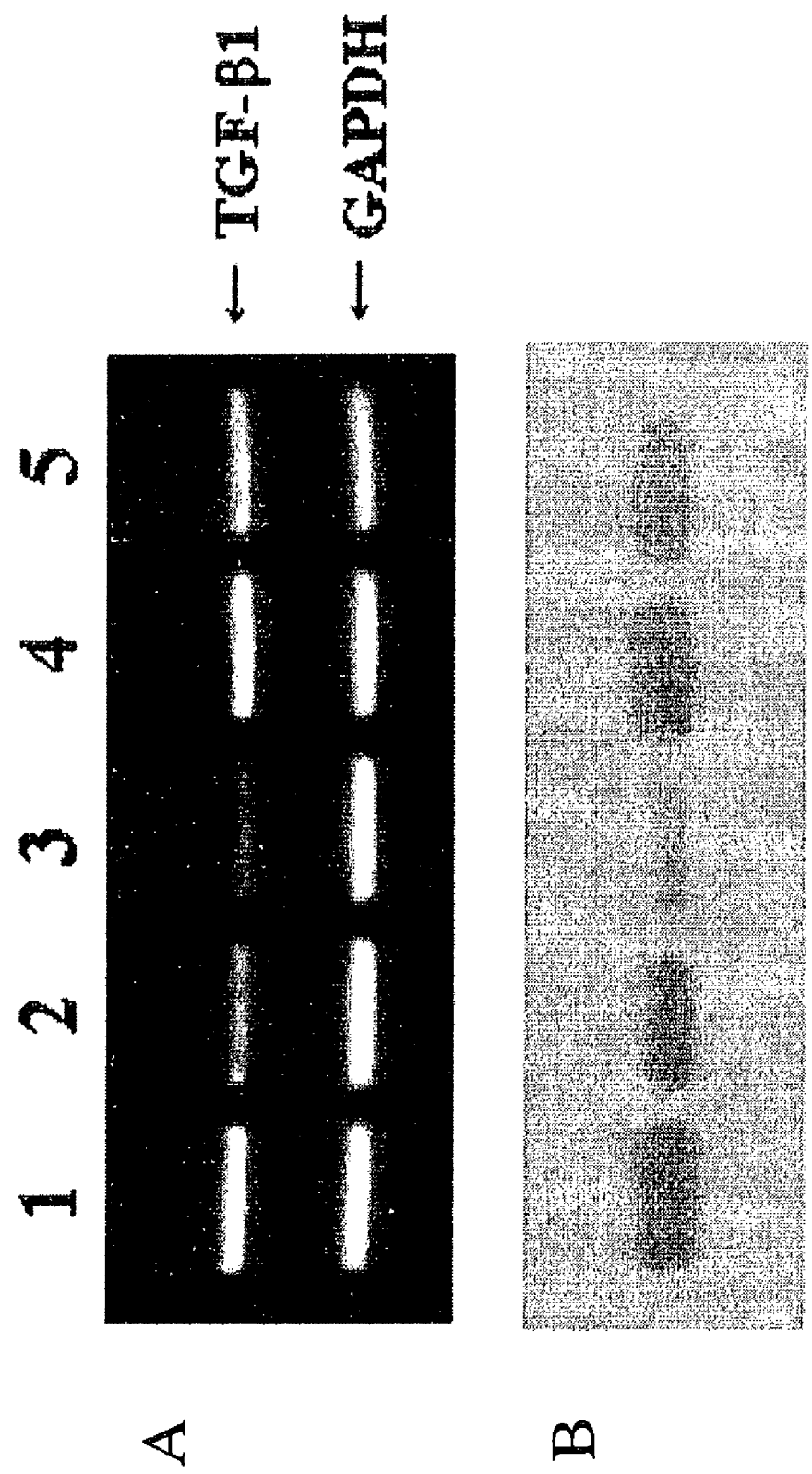
FIGS. 3A-3B show specific reduction of TGF-β1 mRNA by TGF-β1 RiAS. Cells were transfected with a triple complex of oligos (0.1 or 0.3 μg)-tat-liposomes and were later used for RT-PCR assay. (A) RT-PCR was preformed to examine antisense activity of TGF-β1 RiAS. (B) Bands shown in the lower panel are the result of Southern blotting probed with an internal hybridizing primer. Lane 1; Sham, lane 2; 0.1 μg TGF-β1 RiAS, lane 3; 0.3 μg TGF-β1 RiAS, lane 4; 0.1 μg SC RiAS, lane 5; 0.3 μg SC RiAS.

We next examined if TGF-β1 RiAS is effective in the elimination of the target mRNA in a sequence-specific manner. TGF-β1 RiAS was complexed with the tat peptide and liposomes to improve transfection efficiency. H4-IIE rat hepatoma cells were transfected with either TGF-β1 RiAS or SC RiAS at a concentration of 0.1 or 0.3 μg, respectively, and incubated for 24 hr. Total RNA was isolated from transfected cells, and TGF-β1 mRNA was amplified by RT-PCR to examine the antisense activity of TGF-β1 RiAS. H4-IIE cells that were treated with TGF-β1 RiAS showed reduction of TGF-β1 mRNA by about 30% at 0.1 μg and more than 70% at 0.3 μg, respectively (FIG. 3A). By contrast, when H4-IIE cells were treated with SC RiAS, TGF-β1 expression was not significantly affected. GAPDH expression, shown in the bottom panel of the figure as a control, was not affected by the treatment of TGF-β1 RiAS. These results were confirmed again by Southern blotting using DNA oligos hybridizing to the middle of the amplified DNA fragments (FIG. 3B).

Example 9.3

Efficient Delivery of FITC-Labeled AS Oligos into Renal Tissue

Figure 5:
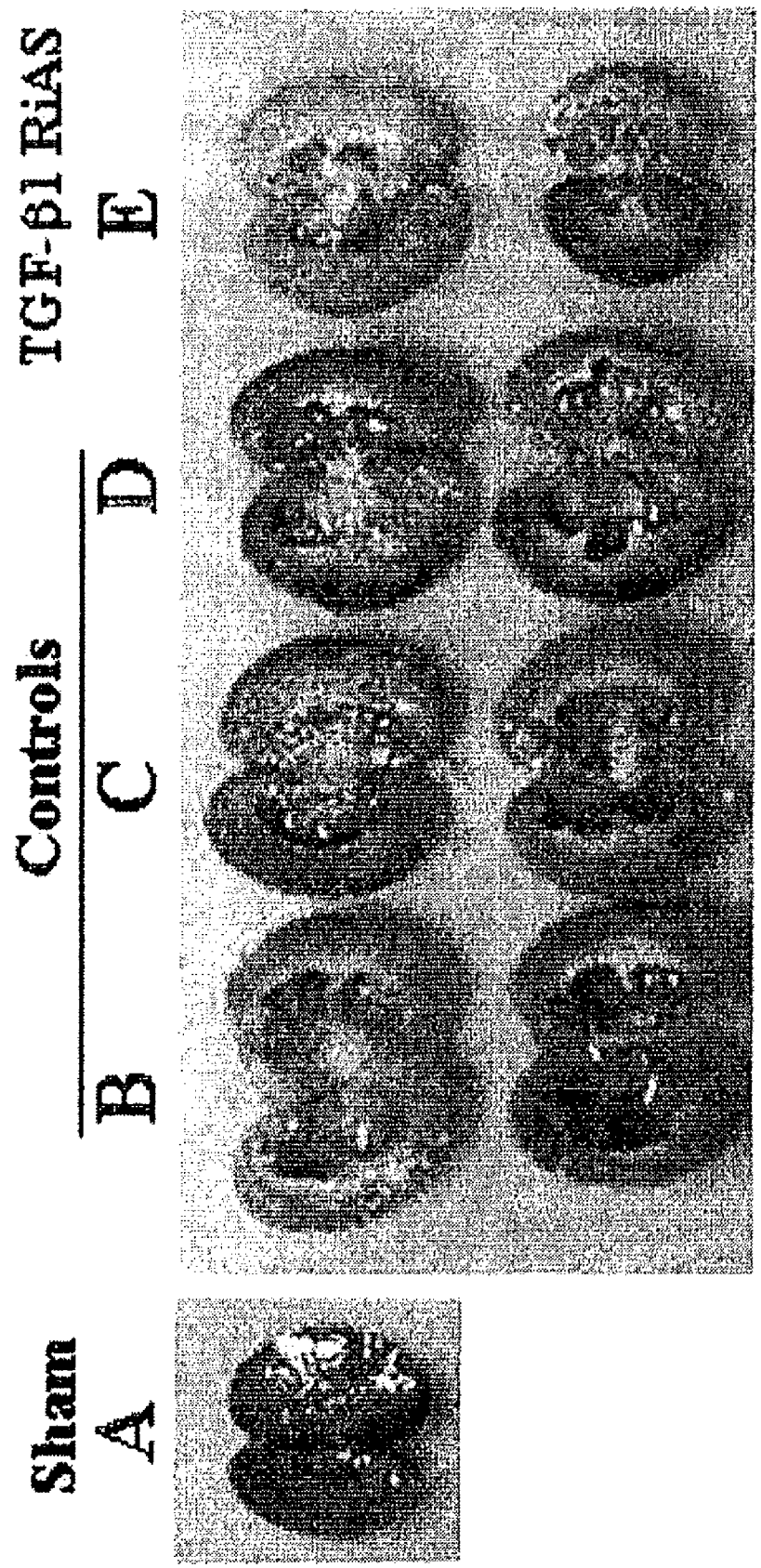
FIG. 5 shows longitudinal dissection of kidneys with UUO in two representative rats. Male SD rats were anesthetized and subjected to TGF-β1 RiAS or control infusion through the ureter. On day 5, the animals were examined and analyzed for morphological changes after longitudinal dissection. A; Naive, B; UUO alone, C; UUO+PBS, D; UUO+SC RiAS, E; UUO+TGF-β1 RiAS.

To achieve successful antisense activity in vivo, it is necessary to have efficient uptake of antisense oligos by target tissues. The 58 mer linear precursor molecules of TGF-β1 RiAS were labeled with FITC and used for in vivo tissue uptake. The FITC labeled antisense oligos of 10 μg were infused into the left kidney through the ureter using a 26-gauge catheter. Kidneys were harvested 6 hr after the Six SD rats were subjected to left proximal ureteral ligation followed by an infusion of TGF-β1 RiAS through the proximal ureter. On day 5, both the left and right kidneys were harvested. They were weighed and the morphology was examined. Kidney weight was expressed as a percent of kidney weight per body weight, and was 0.47%±0.03 in the sham control and was 0.99%±0.10 with UUO. There was a marked increase of kidney weight after the UUO procedure. When the kidney with UUO was treated with TGF-β1 RiAS by ureteral injection, kidney weight per body weight was significantly decreased to 0.68%±0.09 (P<0.005), but was 0.95%±0.08 with PBS alone, and 1.07%±0.12 with the treatment of scrambled RiAS. The results are means±SD of six rats. #P<0.005 in the TGF-β1 RiAS+UUO group versus UUO only, PBS+UUO, and SC RiAS+UUO (Table 2). Control kidneys did not show meaningful difference between each group. Kidneys with the treatment of TGF-β1 RiAS exhibited much less swelling than kidneys with UUO alone, or UUO plus other control treatments (FIG. 5). Further, the longitudinally dissected kidneys of RiAS-treated rats with UUO showed overall preservation of kidney structure, but the kidneys with UUO of control groups showed loss of renal parenchyma in the medullar and the papillary portions of the kidneys.

Example 9.5

Figure 6:
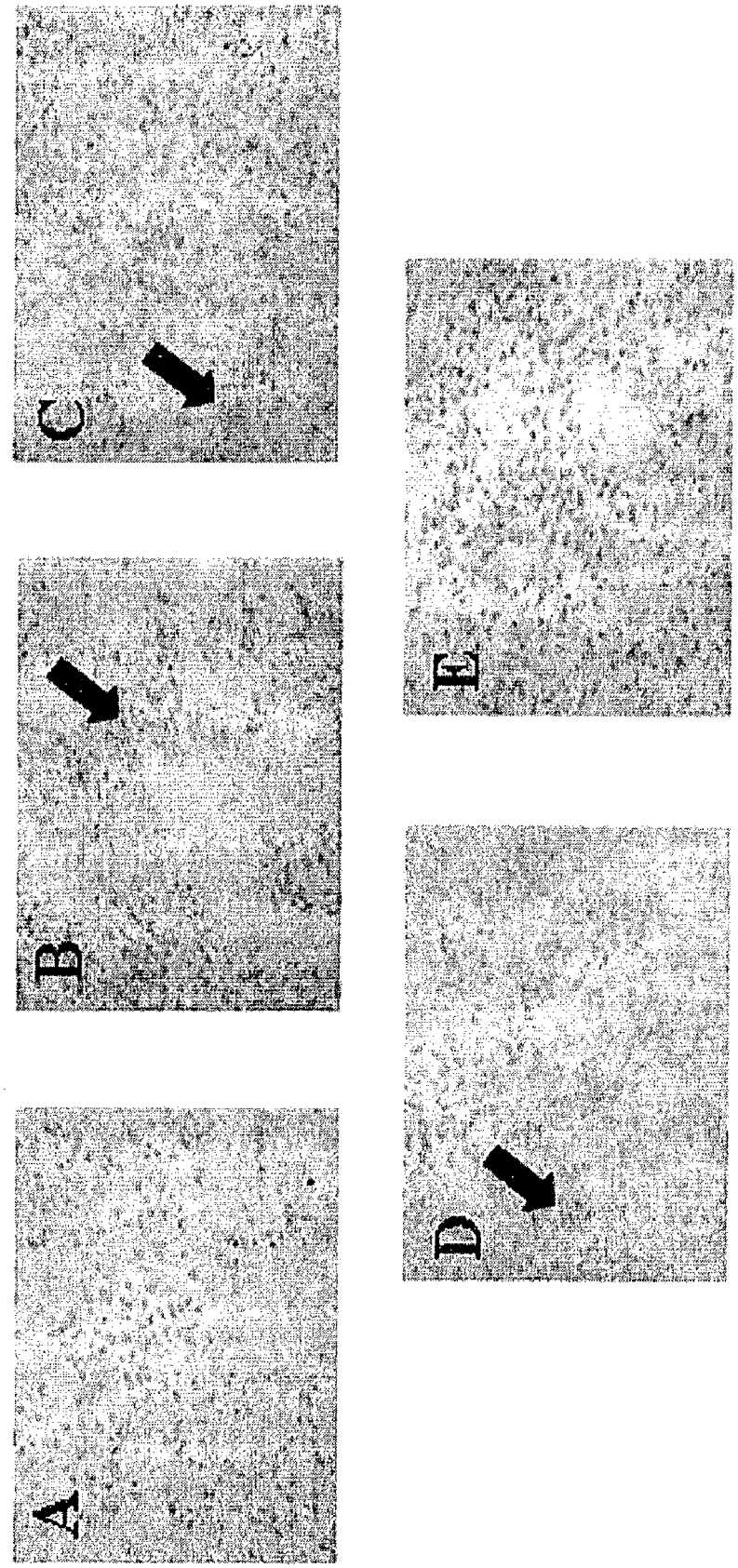
FIGS. 6A-6E show immunohistochemistry for TGF-β1 using anti-TGF-β1 antibodies. Immunohistochemistry was performed with cryosectioned tissue of the kidney. Fixed, dehydrated tissues were mounted with a synthetic mountant for microscopic observation. Brown staining shows the presence of TGF-β1. A; Naive, B; UUO alone, C; UUO+PBS, D; UUO+SC RiAS, E; UUO+TGF-β1 RiAS.
Figure 7:
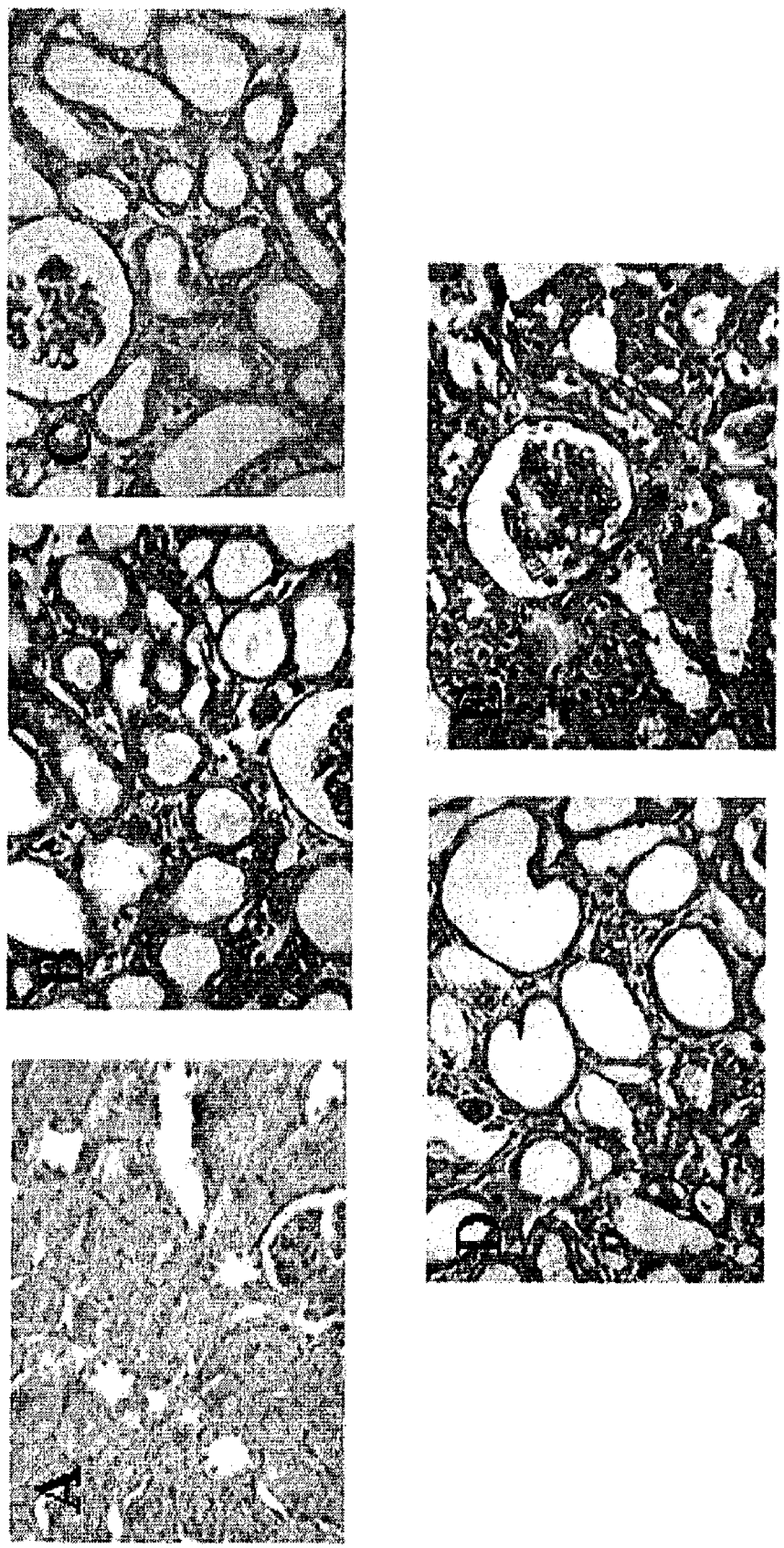
FIGS. 7A-7E show histological observation of tubular atrophy and dilation in kidneys with UUO treated with TGF-β1 RiAS. Tubular atrophy and dilation were shown in sections of the PAS stained tissue. Sections from kidneys following treatment with TGF-β1 RiAS, SC RiAS, PBS, or ureteric obstruction alone are shown for tubular atrophy and dilation. A; Naive, B; UUO alone, C; UUO+PBS, D; UUO+SC RiAS, E; UUO+TGF-β1 RiAS.
Figure 8:
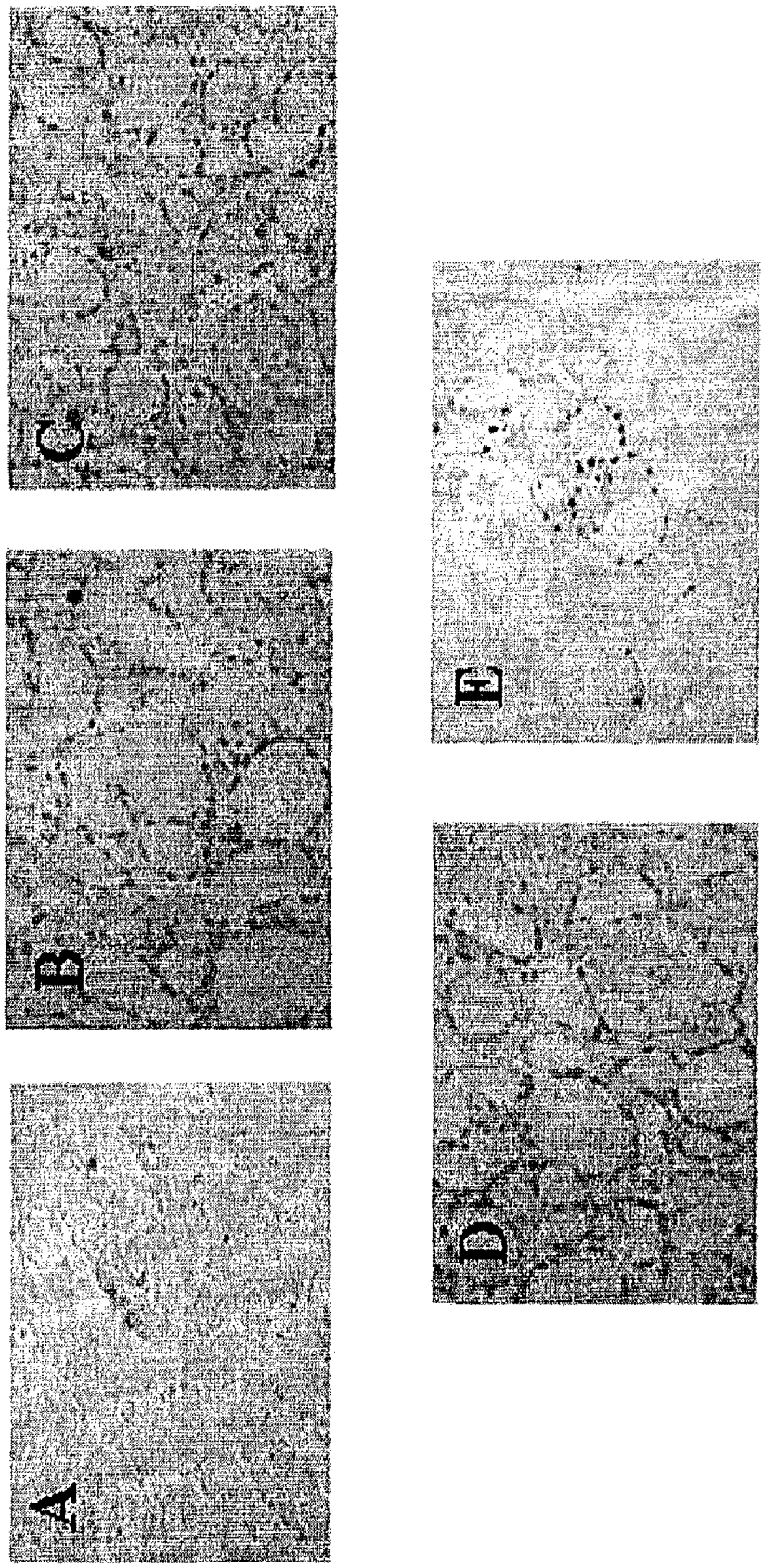
FIGS. 8A-8E show detection of apoptotic cells in kidneys with UUO treated with TGF-β1 RiAS. A TUNEL assay was performed to determine the degree of apoptosis of tubule cells of the kidney. Kidney with UUO was treated with TGF-β1 RiAS, SC RiAS, PBS, or UUO condition alone. A; Naive, B; UUO alone, C; UUO+PBS, D; UUO+SC RiAS, E; UUO+TGF-β1 RiAS.

Preservation of Micro-Structures of the Kidney, Shown by Immunohistochemistry and Histological Analyses We examined sequence specific antisense activity and changes of microscopic structures of the kidney, and observed significant amelioration of global injury to the kidney by TGF-β1 RiAS. Kidneys were harvested from two representative rats in each group with the treatment of TGF- β1 RiAS, SC RiAS, and with a sham-treated control group. Immunohistochemistry was carried out to determine if TGF-β1 expression could be diminished by TGF-β1 RiAS treatment in kidneys with UUO (FIGS. 6A-6E). Immunohistochemistry for TGF-β1 revealed positive brown staining in the obstructed kidney, showing enhanced expression of TGF-β1 in the affected tissue. The positive staining for TGF-β1 protein was similarly detected in the kidneys with UUO treated with PBS and SC RiAS. By contrast, TGF-β1 was found to be much reduced in kidneys with UUO following the treatment with TGF-β1 RiAS (FIG. 6E).

Salient physical characteristics in kidneys with UUO are tubular atrophy and dilation, which are believed to be mediated by enhanced TGF-β1 expression. Light microscopy of PAS-stained renal sections from the kidneys with UUO showed that interstitial spaces of the cortex and the medullar increased in a rapid and progressive manner. A large number of renal tubules were subsequently dilated, and the epithelium was flattened in some tubules (FIGS. 7A-7E). By contrast, sections of control kidneys with UUO treated with PBS, SC RiAS or sham treatment were shown to have extensive tubular atrophy and dilation; a group treated with TGF-β1 RiAS showed significantly diminished dilation and atrophy. As expected, sections from the control kidneys of sham-operated rats appeared normal.

Example 9.6

Reduction of Apoptotic Cell Death Detected by in situ TUNEL Assay

Since kidneys with UUO showed global atrophy and dilation of renal tubules, we determined whether renal tubule cells undergo apoptosis. When kidneys with UUO were treated with TGF-β1 RIAS, apoptotic cells were found to be much less abundant in renal tubular cells, compared with those with other control treatments (FIGS. 8A-8E). Whereas normal kidneys showed apoptosis positive cells at 3±3.3 cells/microscopic field, the kidney with sham treatment showed apoptosis 280.9±24.6 positive cells (400×). TGF-β1 RiAS treatment decreased tubular apoptosis to a level of 21.3±12.1 cells/microscopic field (P<0.001). By contrast, groups with UUO, tubular apoptosis was elevated to a level of 236.8±29.6 cells with SC RiAS treatment, and 260.4±41.3 cells with PBS treatment.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A purified single-stranded covalently closed circular nucleic acid molecule comprising a TGF-β1 specific antisense region, which specifically inhibits expression of TGF-β1,
   wherein the molecule comprises at least two loops separated by a stem structure, wherein at least one loop comprises a target antisense sequence to inhibit TGF-β1expression, and
   wherein said molecule comprises a sequence that is substantially similar to SEQ ID NO:1.

2. A method of making the compound according to claim 1, comprising ligating together at least two linear antisense molecules with stem-loop structure having either or both 5' or 3' ends substantially complementary to each other so that a covalently closed antisense molecule is made.

3. The method according to claim 2, wherein the linear antisense molecules are specific for the same target nucleic acid.

4. A method of inhibiting expression of TGF-β1 comprising contacting a sample comprising TGF-β1 expressing cells with the covalently closed antisense molecule according to claim 1.

5. A method of treating a condition caused by expression of TGF-β1, comprising administering the covalently closed antisense molecule according to claim 1 to a subject in need thereof.

6. The method according to claim 5, wherein said condition is fibrosis.

7. The method according to claim 6, wherein the fibrosis is in the kidney.

8. The method according to claim 6, wherein the fibrosis tubulointerstitial fibrosis.

9. The method according to claim 6, wherein the fibrosis is in the liver.

10. The method according to claim 6, wherein the fibrosis is in the lung.

11. A method for treating unilateral ureteric obstruction comprising administering a composition comprising the covalently closed antisense molecule according to claim 1 to a subject in need thereof.

12. A method of preventing accumulation of extracellular matrix proteins at a site of injury comprising administering the covalently closed antisense molecule according to claim 1 to a subject in need thereof.

13. A method of delivering a covalently closed antisense molecule to a cell, comprising contacting the cell with the covalently closed antisense molecule according to claim 1, a tat or tat-like peptide and a carrier composition.

14. The method according to claim 13, wherein the tat or tat-like peptide and the carrier composition are mixed before contacting the cell.

15. A composition comprising a covalently closed antisense molecule according to claim 1, a tat or tat-like peptide, and a nucleic acid delivery carrier.

16. The composition according to claim 15, wherein the carrier is a liposome.

17. The composition according to claim 16, wherein said liposome is a cationic liposome.

18. A method of inhibiting expression of TGF-β1 comprising contacting a sample comprising TGF-β1 expressing cells with the composition according to claim 15.

19. A method of inhibiting expression of TGF-β1 comprising contacting a sample comprising TGF-β1 expressing cells with the composition according to claim 16.

20. A method of inhibiting expression of TGF-β1 comprising contacting a sample comprising TGF-β1 expressing cells with the composition according to claim 17.

* * * * *